United States Patent [19]

Shaw et al.

[11] Patent Number: 5,166,322
[45] Date of Patent: Nov. 24, 1992

[54] CYSTEINE ADDED VARIANTS OF INTERLEUKIN-3 AND CHEMICAL MODIFICATIONS THEREOF

[75] Inventors: Gray Shaw, Bedford; Geertruida Veldman, Sudbury; Joseph L. Wooters, Brighton, all of Mass.

[73] Assignee: Genetics Institute, Cambridge, Mass.

[21] Appl. No.: 341,990

[22] Filed: Apr. 21, 1989

[51] Int. Cl.$^5$ .................... C07K 13/00; C12N 15/24
[52] U.S. Cl. ................... 530/351; 530/402; 530/404; 530/405; 530/403; 930/141; 435/69.5; 435/69.52; 424/85.1; 424/85.2; 424/85.91; 525/54.1
[58] Field of Search ............ 530/351, 402–406; 435/69.5, 69.52; 424/85.1, 85.2, 85.91; 525/54.1

[56] References Cited

U.S. PATENT DOCUMENTS

| | | | |
|---|---|---|---|
| 3,960,830 | 6/1976 | Bayer et al. | 530/300 |
| 4,002,531 | 1/1977 | Royer | 435/108 |
| 4,055,635 | 10/1977 | Green | 424/94 |
| 4,088,538 | 5/1978 | Schneider | 435/174 |
| 4,179,337 | 12/1979 | Davis et al. | 424/94 |
| 4,261,973 | 4/1981 | Lee et al. | 424/88 |
| 4,301,144 | 1/1981 | Iwashita et al. | 424/78 |
| 4,379,086 | 5/1983 | Kimura et al. | 424/107 |
| 4,412,989 | 11/1983 | Iwashita et al. | 514/762 |
| 4,415,665 | 11/1983 | Mosbach et al. | |
| 4,495,285 | 1/1985 | Shimizu et al. | 435/181 |
| 4,496,689 | 1/1985 | Mitra | 435/181 |
| 4,609,546 | 9/1986 | Hiratani | 514/2 |
| 4,640,835 | 2/1987 | Shimizu et al. | 435/188 |
| 4,703,039 | 10/1987 | Hawiger et al. | 530/333 |
| 4,737,462 | 4/1988 | Mark et al. | 536/27 |
| 4,766,106 | 8/1988 | Katre et al. | 530/351 |
| 4,791,192 | 12/1988 | Nakagawa et al. | 530/397 |
| 4,818,769 | 4/1989 | Nunberg et al. | 514/2 |
| 4,847,325 | 7/1989 | Shadle et al. | 530/351 |
| 4,877,729 | 10/1989 | Clark et al. | 435/172.3 |
| 4,898,824 | 2/1990 | Yip | 435/177 |
| 4,902,502 | 2/1990 | Nitecki et al. | 530/351 |
| 4,959,455 | 9/1990 | Clark et al. | 530/351 |

FOREIGN PATENT DOCUMENTS

| | | |
|---|---|---|
| 154316 | 9/1985 | European Pat. Off. |
| 0147761 | 10/1985 | European Pat. Off. |
| 254172 | 1/1988 | European Pat. Off. |
| WO86/04145 | 7/1986 | PCT Int'l Appl. |
| WO87/00056 | 1/1987 | PCT Int'l Appl. |
| 1469472 | 4/1977 | United Kingdom. |

OTHER PUBLICATIONS

Carlsson et al., *Biochem. J.* 173: 723-37 (1978).
Wingfield et al., *Eur. J. Biochem.* 179:565-71 (1989).
Clark-Lewis et al, *PNAS* 85, pp. 7897-7901, Nov. 1988.
Dunbar et al, *Science*, 1989, pp. 1493-1496.
Boccu et al, *Z. Naturforsch.* 38c, 1983, pp. 94-99.
Katre, et al., *Proc. Natl. Acad. Sci. USA* 84:1487-91 (1987).
Inada et al., *Biochem and Biophys Res Comm* 122:848-50 (1984).
Takahashi et al., *Biochem and Biophys Res Comm* 121:261-65.
Abuchowski et al., *Cancer Biochem Biophys* 7:175-86 (1984).
Takakura et al., *J. Pharm. Sci.* 87:117-21 (1989).
Furukawa et al., *FEBS letters* 121:239-42 (1980).

*Primary Examiner*—Garnette D. Draper
*Attorney, Agent, or Firm*—Luann Cserr; Bruce Eisen

[57] ABSTRACT

Cysteine added variants ("CAVs") of interleukin-3 are provided having one or more cysteine residues substituted for selected naturally occurring amino acid residues, or inserted into the polypeptide sequence, and preferably being further modified by deletion of certain N-terminal amino acids. Such CAVs may be additionally modified by the coupling of sulfhydryl reactive compounds to the introduced cysteine residue(s) without loss of bioactivity to produce selected homogeneously modified IL-3 and improved pharmaceutical compositions containing the same.

9 Claims, 3 Drawing Sheets mpCys10

```
  1                              10
ATG CCT ATG ACT CAA ACT ACT TCT TTA TGC ACT AGT TGG GTA
Met Pro Met Thr Gln Thr Thr Ser Leu Cys Thr Ser Trp Val

25
AAC TGT TCT AAC ATG ATC GAT GAA ATT ATA ACA CAC TTA AAG CAG
Asn Cys Ser Asn Met Ile Asp Glu Ile Ile Thr His Leu Lys Gln

40
CCA CCT TTG CCC TTG CTG GAC TTC AAC AAC CTC AAT GGG GAA GAC
Pro Pro Leu Pro Leu Leu Asp Phe Asn Asn Leu Asn Gly Glu Asp

55
CAA GAC ATT CTG ATG GAA AAT AAC CTT CGA AGG CCA AAC CTG GAG
Gln Asp Ile Leu Met Glu Asn Asn Leu Arg Arg Pro Asn Leu Glu

70
GCA TTC AAC AGG GCT GTC AAG AGT CTG CAA AAT GCA TCA GCA ATT
Ala Phe Asn Arg Ala Val Lys Ser Leu Gln Asn Ala Ser Ala Ile

85
GAG AGC ATT CTG AAA AAT CTG CTG CCA TGT CTC CCC CTG GCC ACA
Glu Ser Ile Ile Lys Asn Leu Leu Pro Cys Leu Pro Leu Ala Thr

100
GCT GCA CCC ACC AGG CAT CCA ATC CAT ATC AAG GAT GGT GAC TGG
Ala Ala Pro Thr Arg His Pro Ile His Ile Lys Asp Gly Asp Trp

115
AAT GAA TTC CGC CGC AAA CTG ACC TTC TAT CTG AAA ACC CTG GAG
Asn Glu Phe Arg Arg Lys Leu Thr Phe Tyr Leu Lys Thr Leu Glu

130
AAT GCT CAG GCT CAG CAG ACC ACC CTG AGC CTC GCG ATC TTC TAG
Asn Ala Gln Ala Gln Gln Thr Thr Leu Ser Leu Ala Ile Phe Stop
```

FIGURE 1

```
  1                                              10
ATG GCT CCT ATG ACT CAA ACT ACT TCT TTA AAA ACT TCT TGG GTA
Met Ala Pro Met Thr Gln Thr Thr Ser Leu Lys Thr Ser Trp Val

25
AAC TGT TCT AAC ATG ATC GAT GAA ATT ATA ACA CAC TTA AAG CAG
Asn Cys Ser Asn Met Ile Asp Glu Ile Ile Thr His Leu Lys Gln

40
CCA CCT TTG CCC TTG CTG GAC TTC AAC AAC CTC AAT GGG GAA GAC
Pro Pro Leu Pro Leu Leu Asp Phe Asn Asn Leu Asn Gly Glu Asp

55
CAA GAC ATT CTG ATG GAA AAT AAC CTT CGA AGG CCA AAC CTG GAG
Gln Asp Ile Leu Met Glu Asn Asn Leu Arg Arg Pro Asn Leu Glu

70
GCA TTC AAC AGG GCT GTC AAG AGT CTG CAA AAT GCA TCA GCA ATT
Ala Phe Asn Arg Ala Val Lys Ser Leu Gln Asn Ala Ser Ala Ile

85
GAG AGC ATT CTG AAA AAT CTG CTG CCA TGT CTG CCC CTG GCC ACA
Glu Ser Ile Ile Lys Asn Leu Leu Pro Cys Leu Pro Leu Ala Thr

100
GCT GCA CCC ACC AGG CAT CCA ATC CAT ATC AAG GAT GGT GAC TGG
Ala Ala Pro Thr Arg His Pro Ile His Ile Lys Asp Gly Asp Trp

115
AAT GAA TTC CGC CGC AAA CTG ACC TTC TAT CTG AAA ACC CTG GAG
Asn Glu Phe Arg Arg Lys Leu Thr Phe Tyr Leu Lys Thr Leu Glu

130
AAT GCT CAG GCT CAG CAG ACC ACC CTG AGC CTC GCG ATC TTC TAG
Asn Ala Gln Ala Gln Gln Thr Thr Leu Ser Leu Ala Ile Phe Stop
```

FIGURE 2 mpCys10

```
        1                                              10
        ATG CCT ATG ACT CAA ACT ACT TCT TTA TGC ACT AGT TGG GTA
        Met Pro Met Thr Gln Thr Thr Ser Leu Cys Thr Ser Trp Val

25
AAC TGT TCT AAC ATG ATC GAT GAA ATT ATA ACA CAC TTA AAG CAG
Asn Cys Ser Asn Met Ile Asp Glu Ile Ile Thr His Leu Lys Gln

40
CCA CCT TTG CCC TTG CTG GAC TTC AAC AAC CTC AAT GGG GAA GAC
Pro Pro Leu Pro Leu Leu Asp Phe Asn Asn Leu Asn Gly Glu Asp

55
CAA GAC ATT CTG ATG GAA AAT AAC CTT CGA AGG CCA AAC CTG GAG
Gln Asp Ile Leu Met Glu Asn Asn Leu Arg Arg Pro Asn Leu Glu

70
GCA TTC AAC AGG GCT GTC AAG AGT CTG CAA AAT GCA TCA GCA ATT
Ala Phe Asn Arg Ala Val Lys Ser Leu Gln Asn Ala Ser Ala Ile

85
GAG AGC ATT CTG AAA AAT CTG CTG CCA TGT CTG CCC CTG GCC ACA
Glu Ser Ile Ile Lys Asn Leu Leu Pro Cys Leu Pro Leu Ala Thr

100
GCT GCA CCC ACC AGG CAT CCA ATC CAT ATC AAG GAT GGT GAC TGG
Ala Ala Pro Thr Arg His Pro Ile His Ile Lys Asp Gly Asp Trp

115
AAT GAA TTC CGC CGC AAA CTG ACC TTC TAT CTG AAA ACC CTG GAG
Asn Glu Phe Arg Arg Lys Leu Thr Phe Tyr Leu Lys Thr Leu Glu

130
AAT GCT CAG GCT CAG CAG ACC ACC CTG AGC CTC GCG ATC TTC TAG
Asn Ala Gln Ala Gln Gln Thr Thr Leu Ser Leu Ala Ile Phe Stop
```

FIGURE 3 m3Cys10

```
                                              10
              ATG ACT CAA ACT ACT TCT TTA TGC ACT AGT TGG GTA
              Met Thr Gln Thr Thr Ser Leu Cys Thr Ser Trp Val

25
AAC TGT TCT AAC ATG ATC GAT GAA ATT ATA ACA CAC TTA AAG CAG
Asn Cys Ser Asn Met Ile Asp Glu Ile Ile Thr His Leu Lys Gln

40
CCA CCT TTG CCC TTG CTG GAC TTC AAC AAC CTC AAT GGG GAA GAC
Pro Pro Leu Pro Leu Leu Asp Phe Asn Asn Leu Asn Gly Glu Asp

55
CAA GAC ATT CTG ATG GAA AAT AAC CTT CGA AGG CCA AAC CTG GAG
Gln Asp Ile Leu Met Glu Asn Asn Leu Arg Arg Pro Asn Leu Glu

70
GCA TTC AAC AGG GCT GTC AAG AGT CTG CAA AAT GCA TCA GCA ATT
Ala Phe Asn Arg Ala Val Lys Ser Leu Gln Asn Ala Ser Ala Ile

85
GAG AGC ATT CTG AAA AAT CTG CTG CCA TGT CTG CCC CTG GCC ACA
Glu Ser Ile Ile Lys Asn Leu Leu Pro Cys Leu Pro Leu Ala Thr

100
GCT GCA CCC ACC AGG CAT CCA ATC CAT ATC AAG GAT GGT GAC TGG
Ala Ala Pro Thr Arg His Pro Ile His Ile Lys Asp Gly Asp Trp

115
AAT GAA TTC CGC CGC AAA CTG ACC TTC TAT CTG AAA ACC CTG GAG
Asn Glu Phe Arg Arg Lys Leu Thr Phe Tyr Leu Lys Thr Leu Glu

130
AAT GCT CAG GCT CAG CAG ACC ACC CTG AGC CTC GCG ATC TTC TAG
Asn Ala Gln Ala Gln Gln Thr Thr Leu Ser Leu Ala Ile Phe Stop
```

CYSTEINE ADDED VARIANTS OF INTERLEUKIN-3 AND CHEMICAL MODIFICATIONS THEREOF

TECHNICAL FIELD

This invention relates generally to interleukin-3 (IL-3) polypeptides modified by the attachment of compounds having sulfhydryl reactive groups, improved methods for producing such modified IL-3 polypeptides and improved compositions containing them. More particularly, the invention relates particularly to modified IL-3, to which sulfhydryl reactive compounds, including polymers, may be attached at selected positions in the polypeptide that have been modified by the insertion of cysteine residues or the substitution of cysteine residues for other residues.

BACKGROUND

The desirability of modifying biologically active and therapeutically useful polypeptides with a variety of compounds, such as the hydrophilic polymer polyethylene glycol (PEG), to enhance their pharmacokinetic properties has been noted. See, e.g., the discussion of the art in this area of polypeptide modification in published PCT patent application WO87/00056, in U.S. Pat. No. 4,179,337, which discloses conjugating water soluble polypeptides such as enzymes and insulin to PEG or PPG, and in U.S. Pat. No. 4,766,106, which discloses conjugating ordinarily water insoluble beta-interferon, interleukin-2, or immunotoxins to PEG homopolymers or polyoxyethylated glycerol. Such modification can reduce adverse immune response to the polypeptide, increase the solubility for use in pharmaceutical preparations and maintain a desirable circulatory level of such polypeptide for therapeutic efficacy.

One problem not addressed by the art in this area involves the extent to which a polypeptide can be modified by attachment of compounds having reactive groups that will covalently bond to certain amino acid residues of the polypeptide For example, modification of a polypeptide with PEG or similar polymers, can result in random attachment of the polymer at the amino terminus of the polypeptide and/or at one or more lysine residues in the amino acid sequence of the protein Because more than one PEG group can attach to the polypeptide, the resultant composition may contain a heterogeneous mixture of "PEGylated" polypeptide; some polypeptides having only one PEGylated site, others having more than one PEGylated site. Such heterogeneity in composition is undesirable for pharmaceutical use. Furthermore, the non-specificity with regard to the site(s) of attachment of compounds such as PEG to the polypeptide can result in loss of biological efficacy of the polypeptide stemming from undesirable attachment to a polypeptide site required for biological activity.

Co-pending, commonly owned U.S. patent application Ser. No. 137,043 now U.S. Pat. No. 4,904,584 entitled SITE-SPECIFIC HOMOGENEOUS MODIFICATION OF POLYPEPTIDES addresses the foregoing by providing materials and methods for site specific covalent modification of polypeptides by lysine insertion, removal, and/or replacement. However, we have determined that the use of lysine as the attachment site for modification, for example, by PEGylation, may be disadvantageous in the case of IL-3 because not all modifications may result in biologically active compounds and because steps must be taken to prevent PEGylation at N-termini in cases where N-terminal PEGylation is not desired.

SUMMARY OF THE INVENTION

This invention provides materials and methods for site specific covalent modification of IL-3 polypeptides, preferably human IL-3 polypeptides, permitting the production of compositions comprising homogeneously cys modified IL-3s and pharmaceutical compositions containing the same. "Homogeneously cys modified" as the term is used herein means substantially consistently modified only at specific, inserted or substituted cysteine residues. A homogeneously modified IL-3 for example, includes an IL-3 composition which is substantially consistently modified at position 6 (using the convention of counting from the N-terminus of the mature protein) by the insertion of cysteine in place of the threonine of natural IL-3, but not at other positions.

Thus, this invention first provides cysteine added variants ("CAVs") of IL-3. CAVs of this invention encompass IL-3 muteins that contain at least one additional cysteine residue compared to the corresponding naturally occurring or previously known IL-3. The cysteine residue(s) are introduced into the peptide structure of the CAVs at one or more amino acid positions in the natural or previously known counterpart. In the case of human IL-3, we have determined that the naturally occurring cysteine residues at positions 16 and 84 form a disulfide bridge, essential to preserving the desired biological activity of the polypeptide. For the addition of novel cysteines, some positions within the polypeptide, such as position 15 and 51 are unsuitable; cysteines introduced at these positions give rise to human IL-3 polypeptides with substantially reduced biological activity. However, certain substitutions or deletions of residues 1–14 do not significantly diminish the desired biological activity of IL-3. Therefore, a preferred region of novel cysteine introduction into the polypeptide is within positions 1–14 inclusive. Currently, positions 6–12 inclusive are especially preferred sites for cysteine introduction. The subsequent attachment of sulfhydryl reactive compounds, including polymers, as discussed below, to the novel cysteines added at selected positions within this region will not result in any significant loss of biological activity.

By "cysteine added variant" as the term is used herein, we mean variants of IL-3 that are modified in amino acid structure relative to naturally occurring or previously known counterparts such that at least one cysteine residue is inserted into the natural or previously known sequence and/or is used to replace a different amino acid within that sequence.

Additionally, the natural IL-3 sequence, with an added initiator methionine for bacterial expression, may be further modified such that the first alanine is deleted at the N-terminus of the mature polypeptide, altering the amino terminal sequence from MET*ALA*PRO to MET*PRO (the "mp" mutein) For the "mp" mutein, such N-terminus modification permits more consistent removal of the N-terminal methionine. As is already known, in bacterial expression systems, cleavage at the N-terminal methionine occurs.

Alternatively, the natural IL-3 sequence may be further modified such that the first two amino acids at the N-terminus of the mature polypeptide are deleted, leaving a terminus beginning with MET*THR*GLN*THR* (the "m3" mutein). For the "m3" mutein, such N-terminus modification permits one to take advantage of the methionine at position 3 in the naturally occurring human IL-3 molecule, as the initiator methionine.

The CAVs of this invention make it possible to produce homogeneous, biologically active IL-3 compositions substantially specifically and consistently modified at selected positions with sulfhydryl reactive compounds (described hereinafter).

In the practice of this invention, at least one cysteine residue is introduced in that portion of the IL-3 polypeptide where modification via a sulfhydryl reactive compound is desired. The cysteine residue or residues are so introduced by genetic engineering methods as described below. Novel cysteine residues may be engineered into the polypeptide for example, by simple insertion of a cysteine codon into the DNA molecule at the desired site or by converting a desirably located asparagine or other codon to a cysteine codon. Convenient methods for site specific mutagenesis or DNA synthesis for producing a DNA molecule encoding the desired CAV, expression in procaryotic or eucaryotic host cells of the DNA molecule so produced, and recovery of the CAV produced by such expression are also disclosed.

The CAVs of this invention retain useful biological properties of the natural or previously known IL-3 and may thus be used for applications identified for the non-modified parent protein Modification with such sulfhydryl reactive compounds, however, is preferred Such biologically active, modified CAVs can be produced in homogeneous compositions which, it is contemplated, will provide improved pharmacokinetic profiles and/or solubility characteristics relative to the parent polypeptides. Furthermore, CAVs may enable the formation of multimeric forms of the normally monomeric polypeptide with the same, albeit improved characteristics. Multimeric CAVs also enable the formation of "hetero-conjugates"—i.e., two or more distinct polypeptides joined via the sulfhydryl groups of the added cysteine residue s, e.g ., IL-3 joined to EPO (erythropoietin) or IL-3 joined to G-CSF (granulocyte colony-stimulating factor).

Biological activity of the CAVs before or after modification with the sulfhydryl reactive compounds may be determined by standard in vitro or in vivo assays conventional for measuring activity of the parent polypeptide. Alternatively, we provide herein a "small scale" screening method wherein successful Cys modification and attachment of the sulfhydryl reactive compound may be tested.

Selective and homogeneous modification of the CAVs with sulfhydryl reactive compounds is possible since such compounds will covalently bond primarily only to the cysteine residue(s) in the CAV. Secondary reactivity at His, Lys and Tyr residue(s) may be observed, depending on the choice of sulfhydryl reactive compound, but at a significantly lower rate The modified CAVs so produced may then be recovered, and if desired, further purified and formulated into pharmaceutical compositions by conventional methods.

Sulfhydryl reactive compounds include compounds such as polyalkylene glycol, e.g. polyethylene and polypropylene glycol, as well as derivatives thereof, with or without coupling agents or derivatization with coupling or activating moieties, for example, with thiol, triflate, tresylate, aziridine or oxirane, or preferably with S-pyridyl or maleimide moieties. Compounds such as S-Pyridyl Monomethoxy PEG and Maleimido Monomethoxy PEG are exemplary. Additionally, sulfhydryl reactive compounds include, but are not limited to, charged or neutral polymers of the following types dextran, colominic acids or other carbohydrate based polymers, polymers of amino acids and biotin derivatives, resulting in a protein modified with this well known affinity reagent often used for antibody based assays.

Briefly, the method comprises reacting the CAV with a sulfhydryl reactive compound under suitable conditions, preferably non-denaturing conditions, and in sufficient amounts permitting the covalent attachment of the sulfhydryl reactive compound to the introduced cysteine residue(s) present in the polypeptide backbone of the CAV. The reaction may be reducible or non-reducible; and generally, the amount of sulfhydryl reactive compound used should be at least equimolar to the number of cysteines to be derivatized, although use of excess sulfhydryl reactive compound is preferred, both to improve the rate of reaction and to insure consistent modification at all reactive sites. The modified CAV produced, may then be recovered, purified and formulated by conventional methods. See e.g., WO 87/00056 and references cited therein Other aspects of the present invention include therapeutic methods of treatment and therapeutic compositions which employ the modified IL-3 CAVs of the present invention, either alone or with other lymphokines, hematopoietins and/or growth factors, such as granulocyte macrophage colony-stimulating factor (GM-CSF), G-CSF, macrophage colony-stimulating factor (M-CSF), EPO, IL-1, IL-2, IL-4, IL-5, and IL-6. These methods and compositions take advantage of the improved pharmacokinetic properties of these modified CAVs to provide treatments, e.g., such as employing lower dosages of polypeptide, less frequent administration, lower immunogenicity and more desirable distribution, required for the therapeutic indications for the natural polypeptide.

Other aspects and advantages of the present invention will be apparent upon consideration of the following detailed description of the invention, including illustrative examples of the practice thereof.

BRIEF DESCRIPTION OF THE DRAWINGS

FIG. 1 is the human IL-3 gene construct for $E.$ $coli$ expression, having the polypeptide sequence shown of natural (wild type) human IL-3, plus an initiator methionine, as expressed in $E.$ $coli,$ with the amino acids numbered from the N-terminus for reference to the muteins discussed herein FIG. 2 is the "mp" modified polypeptide sequence of the IL-3 of FIG. 1, having the N-terminus modified in accordance with this invention as shown, with amino acids numbered for reference FIG. 3 is the "m3" modified polypeptide sequence of the IL-3 of FIG. 1, having the N-terminus modified in accordance with this invention as shown with amino acids numbered for reference.

DETAILED DESCRIPTION OF THE INVENTION

The present invention involves the selective modification of IL-3 for pharmaceutical use, to both enhance its pharmacokinetic properties and provide homogeneous compositions for human therapeutic use. Although human IL-3, DNA and peptide sequences are preferred as the starting point in this invention, any primate IL-3 is susceptible to use in the method of the invention, given the significant homology between e.g., human and gibbon species of the protein and DNA. See Leary et al., *Blood* (1982) 70: 1343–1348. The method for selectively modifying primate IL-3 involves selecting locations in the polypeptide sequence for the attachment of sulfhydryl reactive compounds. This step may be accomplished by altering the amino acid sequence of the polypeptide by inserting cysteine residues at selected sites or by converting selected endogenous residues into cysteine residues. For example, the codons AAA or AAG, which code for lysine, can be changed to the codon TGC or TGT, which code for cysteine.

CAVs in accordance with this invention also include allelic variations in the IL-3 sequence, i.e. sequence variations due to natural variability from individual to individual, or with other amino acid substitutions or deletions which still retain desirable biological properties of the parent.

All CAVs of this invention may be prepared by expressing recombinant DNA sequences encoding the desired variant in host cells, e.g. procaryotic host cells such as *E. coli*, or eucaryotic host cells such as yeast or mammalian host cells, using methods and materials, e.g. vectors, as are known in the art. Host cells containing and capable of expressing the CAV-encoding DNA are thus emconpassed by this invention. DNA sequences encoding the variants may be produced synthetically or by conventional site-directed mutagenesis of DNA sequences encoding the protein or polypeptide or analogs thereof. FIG. 1 shows the human IL-3 gene construct inserted in plasmid pAL-hIL3-781 and expressed in the *E. coli* K12 strain designated GI586. This strain containing the plasmid was deposited with the American Type Culture Collection, 12301 Parklawn Drive, Rockville, Md. 20852 USA on Apr. 19, 1989 and given accession number 67932. Other DNA sequences for natural primate IL-3 have been cloned and the DNA sequences, including cDNA sequences, and specific peptide sequences for the same have been published, in PCT application number U.S. 87/01702, published as WO 88/00598 on Jan. 28, 1988, and are therefore known in the art. These DNA sequences have been deposited with the American Type Culture Collection and given accession numbers ATCC 67154, 67326, 67319 and 40246.

DNA molecules encoding natural human IL-3s therefore may be obtained (i) by cloning in accordance with the published methods, (ii) from the deposited plasmids, or (iii) by synthesis, e.g. using overlapping synthetic oligonucleotides based on the published sequences which together span the desired coding region. Such methods are known in the art. See the foregoing PCT application published as WO 88/00598 and PCT application number U.S.88/00402 published as WO88/06161.

As mentioned above, DNA sequences encoding individual CAVs of this invention may be produced synthetically or by conventional site-directed mutagenesis of a DNA sequence encoding the parental IL-3 or analogs thereof. Such methods of mutagenesis include the M13 system of Zoller and Smith, *Nucleic Acids Res.* (1982) 10:6487–6500; *Methods Enzymol.* (1983) 100:468–500; and DNA (1984) 3:479–488, which uses single stranded DNA and the method of Morinaga et al., *Bio/technology* (July 1984) 636–639, which uses heteroduplexed DNA. Exemplary oligonucleotides used in accordance with such methods are described below. It should be understood, of course, that DNA encoding each of the CAVs of this invention may be analogously produced by one skilled in the art through site-directed mutagenesis using appropriately chosen oligonucleotides.

The new DNA sequences encoding the CAVs of this invention can be introduced into appropriate vectors for heterologous expression in the desired host cells, whether procaryotic or eucaryotic. The activity produced by the transiently transfected or stably transformed host cells (or their progeny) may be measured by using standard assays conventional for the parental protein. Where the host cell is bacterial, the DNA should be free of introns, e.g. a cDNA or synthetic DNA, and may be free of any secretory leader sequence. For eucaryotic expression, introns may be present or absent and a secretory leader sequence should preferably be present.

The CAVs produced by expression in the genetically engineered host cells may then be purified, and if desired formulated into pharmaceutical compositions by conventional methods, often preferably by methods which are typically used in purifying and/or formulating the parental protein. It is contemplated that such pharmaceutical compositions containing the CAV in admixture with a pharmaceutically acceptable carrier will possess similar utilities to those of the parental proteins, such as those set forth in WO 88/00598 supra, at page 3.

In another, and preferred, aspect of this invention, the CAVs produced by recombinant means as mentioned above are reacted with the desired sulfhydryl reactive compound under conditions permitting attachment of the sulfhydryl reactive moiety to the sulfhydryl group of the introduced cysteine residues in the peptide backbone of the CAV. These modified CAVs, preferably produced initially on a small scale, may then be screened for bioactive muteins possessing the sulfhydryl reactive compounds attached to the site or sites desired. Alternatively, this screening may be accomplished before attachment with the sulfhydryl reactive compound.

The term "sulfhydryl reactive compound" is defined herein as any compound having, or capable of being activated to have, a reactive group capable of forming a covalent attachment to the sulfhydryl group (-SH) of the cysteine residue. Included among such compounds are polymers such as PEG and polypropylene glycol (PPG), dextran, colominic acids or other carbohydrate based polymers and polymers of amino acids and biotin derivatives. Activation may occur by modification of the compound with a sulfhydryl moiety, such as a sulfhydryl group, thiol, triflate, tresylate, aziridine or oxirane, or preferably, with S-pyridyl or maleimide. The sulfhydryl reactive compound need not have any particular molecular weight, but a molecular weight of between about 1,000 and 30,000 for the activated compound is preferred, especially for PEG. Methods of attachment will be described in detail below By controlling the number and location of the cysteines in the CAV sequence, the number and location(s) of the attached sulfhydryl reactive compound can be selectively controlled Such control of attachment location and number enables the production of only certain selectively modified molecules retaining the desired biological activity, rather than production of a heterogeneous mixture of variably modified molecules, only some of which may be active. It is also important to note that this positional selectivity of the PEGylation or other attachment allows the normal functional interactions of the protein to be preserved, blocked, or regenerated by release of the sulfhydryl reactive compound.

Another aspect of the invention is therefore homogeneous compositions of modified IL-3 CAVs as described herein, e.g. PEGylated CAVs. Specific embodiments of IL-3 CAVs of the invention include human IL-3 which has a cysteine residue replacing lysine at position 10 and the m3 initiation sequence. (Amino acid numbers for the CAVs of the present invention are used herein in the conventional manner, sequentially from the N-terminus, and correlate with the numbering system used in FIG. 1 for the natural human IL-3 as expressed in *E. coli.*) Similarly, the naturally occurring lysine residue in human IL-3 (FIG. 1) at amino acid position 100 may be converted to a cysteine to create a human IL-3 CAV of the invention. Another embodiment has cysteine at positions 9 and 10 and the m3 initiation sequence.

For bacterial expression where the secretory leader-encoding DNA sequence is removed from the CAV-encoding DNA, it may be desirable to additionally modify the sequence such that it encodes an N-terminus comprising Met-Pro- - - (the mp mutein) instead of other N-termini such as Met-Ala-Pro. Such N-terminal modification permits more consistent removal of the N-terminal methionine. Alternatively, the first two residues of natural, human IL-3 may be deleted, leaving the naturally occurring methionine at position 3 as the translation initiator (the m3 mutein).

CAVs of this invention, modified as described, encompass CAVs containing other modifications as well, including truncation of the peptide sequence, deletion or replacement of additional amino acids with amino acids other than cysteine, insertion of new N-linked glycosylation sites, abolishment of natural N-linked glycosylation sites, etc., so long as the bioactivity of the molecule is retained. Thus, this invention encompasses CAVs encoded for by DNA molecules which are capable of hybridizing under stringent conditions to the DNA molecule encoding the parental IL-3 (or would be so capable but for the use of synonymous codons) so long as the encoded polypeptide contains one or more additional introduced cysteine residues relative to the parental peptide sequence.

Because the method and compositions of this invention provide homogeneous modified IL-3s, the invention also encompasses such homogeneous compositions for pharmaceutical use which comprise a therapeutically effective amount of a modified CAV described above in admixture with a pharmaceutically acceptable carrier. Such composition can be used in generally the same manner as that described for the natural or recombinant polypeptides. It is contemplated that the compositions will be used for treating a variety of conditions, e.g. involving stimulating hematopoietis or improving a patient's hematological profile. For example, a modified IL-3 of the present invention may be used as an adjunct to cancer chemotherapy or in the treatment of immune disorders, as discussed in WO 88/00598, at page 17-19. The exact dosage and method of administration will be determined by the attending physician depending on the particular modified CAV employed, the potency and pharmacokinetic profile of the particular compound as well as on various factors which modify the actions of drugs, for example, body weight, sex, diet, time of administration, drug combination, reaction sensitivities and severity of the particular case. Generally, the daily regimen should be in the range of the dosage for the natural or recombinant unmodified IL-3, e.g. a range of about 0.1 to about 100 μg of polypeptide per kilogram of body weight, preferably from about 0.1 to about 30 μg of polypeptide per kilogram of body weight.

The therapeutic method and compositions of the present invention may also include co-administration with other drugs or human factors. A non-exclusive list of other appropriate hematopoietins, CSFs (colony stimulating factors) and interleukins for simultaneous or serial co-administration with the CAVs of the present invention includes GM-CSF, CSF-1 (in its various known forms; CSF-1 is also referred to as M-CSF or macrophage colony-stimulating factor), G-CSF, Meg-CSF, EPO, IL-1, IL-2, IL-4, IL-6, B-cell growth factor, B-cell differentiation factor and eosinophil differentiation factor. Additionally, the CAVs of the present invention may be administered with, or chemically attached to, monoclonal or polyclonal antibodies in a therapeutic use. Alternatively, these growth factors may be attached to certain toxins, e.g., ricin, for use in a therapeutic regimen. The dosage recited above would be adjusted to compensate for such additional components in the therapeutic composition or regimen. In the case of pharmaceutical compositions containing modified lymphokine CAVs, for example, progress of the treated patient can be monitored by periodic assessment of the hematological profile, e.g. white cell count, hematocrit and the like.

The following examples illustratively describe the CAVs and the methods and compositions of the present invention.

EXPERIMENTAL MATERIALS, METHODS AND EXAMPLES

EXAMPLE 1

Eucaryotic Expression Materials and Methods

Eukaryotic cell expression vectors into which DNA sequences encoding CAVs of this invention may be inserted (with or without synthetic linkers, as required or desired) may be synthesized by techniques well known to those skilled in this art. The components of the vectors such as the bacterial replicons, selection genes, enhancers, promoters, and the like may be obtained from natural sources or synthesized by known procedures. See Kaufman et al., *J. Mol. Biol.*, (1982) 159:601-621; Kaufman, *Proc. Natl. Acad. Sci.* (1985) 82:689-693. See also WO 87/04187, filed Jan. 2, 1987 (pMT2 and pMT2-ADA), and U.S. patent application Ser. No. 88,188, filed Aug. 21, 1987 now abandoned (pxMT2). Exemplary vectors useful for mammalian expression are also disclosed in the patent applications cited in Example 4, which are hereby incorporated by reference. Eucaryotic expression vectors useful in producing variants of this invention may also contain inducible promoters or comprise inducible expression systems as are known in the art. See U.S. patent application Ser. No. 893,115 (filed Aug. 1, 1986) now abandoned and PCT/U.S.87/01871, published as WO88/00975 on Feb. 11, 1988.

Established cell lines, including transformed cell lines, are suitable as hosts. Normal diploid cells, cell strains derived from in vitro culture of primary tissue, as well as primary explants (including relatively undifferentiated cells such as hematopoietic stem cells) are also suitable. Candidate cells need not be genotypically deficient in the selection gene so long as the selection gene is dominantly acting.

If eucaryotic host cells are used, they will preferably will established mammalian cell lines. For stable integration of the vector DNA into chromosomal DNA, and for subsequent amplification of the integrated vector DNA, both by conventional methods, CHO (Chinese Hamster Ovary) cells are presently preferred in such embodiments Alternatively, the vector DNA may include all or part of the bovine papilloma virus genome (Lusky et al., Cell (1984) 36: 391–401) and be carried in cell lines such as C127 mouse cells as a stable episomal element. Other usable mammalian cell lines include HeLa, COS-1 monkey cells, melanoma cell lines such as Bowes cells, mouse L-929 cells, 3T3 lines derived from Swiss, Balb-c or NIH mice, BHK or HaK hamster cell lines and the like.

Stable transformants then are screened for expression of the CAV product by standard immunological or activity assays. The presence of the DNA encoding the CAV IL-3s may be detected by standard procedures such as Southern blotting. Transient expression of the CAV genes during the several days after introduction of the expression vector DNA into suitable host cells such as COS-1 monkey cells is measured without selection by activity or immunologic assay of the proteins in the culture medium.

Following the expression of the DNA by conventional means, the CAVs so produced may be recovered, purified, and/or characterized with respect to physicochemical, biochemical and/or clinical parameters, all by known methods.

EXAMPLE 2

Bacterial and Yeast expression

Bacterial and yeast expression may be effected by inserting (with or without synthetic linkers, as required or desired) the DNA molecule encoding the desired CAV into a suitable vector (or inserting the parental DNA sequence into the vector and mutagenizing the sequence as desired therein), then transforming the host cells with the vector so produced using conventional vectors and methods as are known in the art, e.g. as disclosed in published PCT Application No. WO 86/00639, published Jan. 30, 1986. Transformants are identified by conventional methods and may be subcloned if desired. Characterization of transformants and recombinant product so produced may be effected and the product recovered and purified, all as described in Example 1.

For bacterial expression, the DNA sequences encoding the CAVs are preferably modified by conventional procedures to encode only the mature polypeptide and may optionally be modified to include preferred bacterial codons.

Expression in E. coli

The CAVs of Example 5 were expressed in E. coli as follows: Plasmid pAL-hIL3-781 was transformed into an E. coli K12 strain GI586, a derivative of strain W3110 in which the $C_I$ and Rex regions of bacteriophage lambda carrying the $C_I857$ allele have been inserted into the ClaI site of the lacZ gene of the bacterial genome. This insert consists of all of the DNA sequences between nucleotides 35711 and 38104 of the phage genome. See F. Sanger, et al., J. Mol. Biol. (1982) 162:729. E. coli K12 strain GI586 (pAL-hIL3-781) was deposited at the ATCC on Apr. 19, 1989 and given accession number 67932.

When GI586 transformed with pAL-hIL3-781 is grown at 30 degrees centigrade to high cell density and then heated to 40 degrees centigrade, IL-3 is produced rapidly and accumulates over the next two or three hours to reach greater than 10 percent of the total cellular protein. This protein is produced in an insoluble form which must be solubilized and refolded by conventional methods See, e.g., T. E. Creighton, Prog. Biophys. Molec. Biol. (1978) 33:231–297. Following expression, the CAVs so produced were recovered, purified and characterized as follows.

1. Purification of CAV IL-3

All buffers were prepared using glass distilled water; all were degassed for at least five minutes, using house vacuum/sonification, prior to the addition of DTT.

First, 400 grams wet weight frozen E. coli cell paste was suspended in 2500 ml of buffer containing 50 mM Tris-HCl, pH 8.5, 1 mM EDTA, 5 mM P-aminobenzamidine, 1 mM PMSF and 2 mM DTT (hereinafter in this Example "buffer A"), to obtain a final volume of 2850 ml. Glass rods and magnetic stirrers were used to resuspend the cell paste. Then the cell suspension was lysed by passing it through a matin gaulin valve at 9000 psi four times, with cooling between each time. Temperature was maintained below 30 degrees centigrade by collection of the lysate into glass vessels cooled in ice/water mixture. Protein concentration was 22 mg/ml; final volume was 2850 ml.

The lysate was centrifuged for 30 minutes at 8000 rpm in a Sorval centrifuge with a GS-3 rotor. The supernatant (2600 ml at 17.0 mg/ml) was discarded and the resultant pellet (hereinafter in this Example P1) from this centrifugation was resuspended in approximately 400 ml buffer A, using glass rods and a magnetic stirrer. The milky suspension was then passed through an 18 gauge needle using a 60 ml syringe The final volume was 640 ml, with a protein concentration of 25.6 mg/ml.

The resuspended P1 pellet was then centrifuged for 10 minutes in a Sorval centrifuge with a GS-3 rotor at 8000 rpm. The supernatant from this centrifugation was poured into two fresh centrifuge tubes (hereinafter in this example "S2") and the resultant pellet ("P2") was resuspended in buffer A to a final volume of 165 ml, with a protein concentration of 50 mg/ml. The S2 supernatant was then centrifuged for 10 minutes and the resulting pellet ("P3") was resuspended in 65 ml buffer A. The resulting supernatant ("S3") was further centrifuged for 10 minutes and the resulting P4 pellet was resuspended in buffer A to a final volume of 50 ml, with a protein concentration of 11.3 mg/ml. Because the P4 pellet contained so little IL-3, it was not used in subsequent steps. The S4 supernatant from the final centrifugation, approximately 600 ml, contained the membranous components at a concentration of approximately 10 mg/ml.

The P2 and P3 pellets were pooled and centrifuged at 9000 rpm (GSA rotor) for 10 minutes yielding two pellets ("P2-2") and a cloudy supernatant, which using HPLC analysis was found void of IL-3 and was discarded. The P2-2 pellet was frozen at −20 degrees centigrade for later use.

The frozen P2-2 pellet was then resuspended in buffer A (which contained 10 mM DTT rather than 2 mM DTT) to a final volume of 100 ml using glass rods and magnetic stirrer and then passed through an 18 gauge needle. 400 ml of 7M fresh guanidine in the 10 mM DTT buffer A was added to the resuspended P2-2 and after one quick inversion, the solubilized P2-2 pellet was immediately placed in 3×250 centrifuge tubes and centrifuged for 15 minutes at 8000 rpm (GSA rotor). 500 ml of the supernatant at a concentration of 5.98 mg/ml was purified further at room temperature by RP-HPLC. The foregoing two steps were performed in 17 to 22 minutes 2. RP-HPLC separation of IL-3 CAVs The buffers used in this separation protocol were 0.1% (v/v) TFA in water, and 0.1% TFA in acetonitrile.

A two inch Vydac C4 column was equilibrated in 10% acetonitrile. The supernatant from the 7M guanidine solubilization was immediately applied onto the C4 column having a volume of approximately 470 ml at 180 ml per minute. The column was developed at 20 ml per minute and was washed in 10% acetonitrile until absorbance at 280 nm was back to baseline. The following gradient was established by washing with the following concentrations of acetonitrile at the following times:

| time (in minutes) | % acetonitrile |
| --- | --- |
| 5 | 10 |
| 10 | 35 |
| 55 | 55 |
| 60 | 80 |
| 65 | 80 |
| 67.5 | 10 |

40 ml fractions were collected after 35 minutes into the gradient. 10 µl samples were removed from each fraction, vacuum speed dried and taken up in 20 µl of 2x SDS-sample Laemmli buffer. SDS-PAGE analysis was performed and IL-3 presence was confirmed. All fractions were then frozen at −80 degrees centigrade.

3. Refolding of IL-3 CAVs

One of the RP-HPLC separated fractions containing approximately 75 mg (7.5 ml) IL-3 was diluted to approximately 0.5 mg/ml by the addition of 142.5 ml of 6.4M guanidine in 50 mM NaPO$_4$ 7.0, 1mM EDTA and 0.2 mM DTT. The mixture was then added to 750 ml of 50 mM Na PO$_4$ pH7, 1 mM EDTA, 0.2 mM DTT buffer, transferred to dialysis tubing and dialyzed for two hours against 4 L of the same buffer. The IL-3 (now approximately 0.22M guanidine) was twice further dialyzed against 8 L of the same buffer containing 0.1 mM DTT.

PEGylation of this purified IL-3 is set forth in Examples 7 and 8 below.

4. Confirmation of bioactivity

Bioactivity of the IL-3 CAV may be confirmed by using the TF-1 cell proliferation assay. The TF-1 cell line has been described (Kitamura et al., *Blood* (1989) 73:375-380). Cells are maintained at 37 degrees centigrade in humid air containing 5% $CO_2$ and culture media used is RPMI (Gibco), 10% heat inactivated fetal calf serum, 2 mM L-glutamine, with 5 ng/ml of recombinant GM-CSF added. Every 3-4 days cells are adjusted to a density of 2×10$^5$ cells/ml Just prior to assay the cells are centrifuged 500xG, 5 minutes, washed in culture media without rGM-CSF, recentrifuged and resuspended at a density of 10$^5$ cells/ml.

IL-3 samples to be assayed are diluted between 1:500 and 1:10,000 in culture media without rGM-CSF. 125 µl of the diluted sample is placed in the top row of a 96 well microtiter plate. The remaining wells are filled with 100 µl of culture media without rGM-CSF and the top row samples are serially diluted five fold down the microtiter plate. To each well, 100 µl of diluted cells (10$^4$ cells) are added and the plate is incubated at 37 degrees centigrade, 5% $C^{O2}$ for 48-72 hours. Thereafter, 0.5 uCi $^3$H-thyidine is added per well and the plate is further incubated for 4-6 hours. Cells are then harvested using an automated cell harvester (LKB 1295-001) and the $^3$H-thymidine uptake is quantitated.

Alternatively, a CML proliferation assay as described in PCT/U.S.87/017024, International Publication Number WO88/00598, published Jan. 28, 1988, can be used.

EXAMPLE 4

Mutagenesis Protocol

Site directed mutagenesis may be effected using conventional procedures known in the art. See e.g., International Applications Nos. WO 87/07144, and WO 87/04722, and U.S. patent application Ser. Nos. 099,938 (filed Sep. 23, 1987) now abandoned and 088,188 (filed Aug. 21, 1987) now abandoned and the references cited therein.

EXAMPLE 5

Exemplary human IL-3 Mutagenesis Reactions

The following human IL-3 muteins were engineered by substitution of the codons indicated for a cys codon, or by insertion of a cys codon, using conventional site directed mutagenesis techniques:

| mp mutein | m3 mutein | cys modification |
| --- | --- | --- |
| mpCys10 | m3cys10 | AAA to TGC (Lys to Cys) |
| mpCys6 | m3Cys6 | ACT to TGC (Thr to Cys) |
| mpCys8 | m3Cys8 | TCT to TGC (Ser to Cys) |
| mpCys12 | m3Cys12 | TCT to TGC (Ser to Cys) |
| mpCys100 | m3Cys100 | AAG to TGT (Lys to Cys) |
| mpCys134 | m3Cys134 | Insertion of TGT between TTC and TAG (Cys between Phe 133 and stop codon) |
| mpCys3 | | ATG to TGC (Met to Cys) |
| mpΔ1Cys19 | | Replacement of amino acids 1-15 with the "mp" terminus and modif. of pos. 19 from ATG to TGC (Met to Cys) |
| | m3Cys6,10 | ACT and AAA to TGC (Thr and Lys to Cys) |
| | m3Cys9,10 | TTA and AAA to TGC (Leu and Lys to Cys) |
| | m3Cys6,8 | ACT and TCT to TGC (Thr and Ser to Cys) |
| | m3Cys6,8,10 | ACT, TCT and AAA to TGC (Thr, Ser and Lys to Cys) |
| | m3Cys8,9,10 | TCT, TTA and AAA to TGC (Ser, Leu and Lys to Cys) |

In the examples depicted above the modification site of the natural IL-3 protein is designated by the number after "Cys" and the amino acid sequence of the CAV is identical to that of the native protein, except for the position indicated, with respect to the N-terminus (see FIG. 1). The "mp" and "m3" designation signify the two different alterations of the N-terminus that will be discussed in detail below. Additionally, cys may be introduced in place of native codons at positions 63 or 66, alone or in combination with other cys introduction(s), e.g. at position 10—with any of the described N-termini.

With respect to IL-3 muteins, certain point modifications may result in partial loss of biological activity or inability of the sulfhydryl reactive compound to attach. For example, modification at position 28 results in a biologically active CAV, but attachment of a sulfhydryl reactive compound fails, possibly because position 28 appears internally in the refolded CAVs tertiary structure Compare, Wingfield, D., et al., *Eur. J. Biochem.* (1989) 179:565-571, in which the authors discussed the Cys modification of IL-1$\beta$ at position 138 to active IL-1$\beta$-phycoerythrin conjugate Additionally, we have found that substitution of a cysteine residue for the amino acids at positions 15 or 51 of the natural human IL-3 may result in partial loss of bioactivity. To test for activity after attachment of the sulfhydryl reactive compound, this invention further provides a "small scale" screening technique to readily determine whether modification and attachment has been successful (see Example 9 below).

The human IL-3 was additionally modified at its N-terminus in two different and alternative configurations, represented by the "mp" and "m3" designations. The "mp" designation indicates a deletion of the first alanine in the natural human IL-3 protein, thereby changing the N-terminal sequence from MET\*ALA\*-PRO to MET\*PRO. Compare FIGS. 1 and 2. The "m3" designation indicates a deletion of the first two amino acids in the natural human IL-3 protein, MET-\*ALA\*PRO, to yield a terminus beginning MET\*THR\*GLU\*THR\*. Compare FIGS. 1 and 3. The reasons for these modifications have already been discussed. With respect to N-terminus modification of the mp$\Delta$1Cys19 mutein, amino acids 1-15 were deleted and replaced with the "mp" terminus.

It should be understood of course that the depicted list of muteins is merely exemplary and not exclusive. The design and synthesis of alternative and additional muteins of both human and gibbon IL-3 in accord with this invention is well within the present skill in the art. Synthesis of such muteins may be conveniently effected using conventional techniques and methods.

One skilled in the art, of course, could readily design and synthesize other muteins for substitution of cysteine codons or insertion thereof in DNA sequences encoding IL-3. To modify more than one site, mutagenesis may be carried out iteratively, or in some cases using an oligonucleotide designed for mutagenesis at more than one site.

EXAMPLE 6

Synthesis of DNA molecules encoding CAVs

As an alternative to the production of CAV-encoding DNA by mutagenesis of the parental IL-3 DNA sequence, it should be understood that the desired CAV-encoding DNA may be prepared synthetically. In that case, it will usually be desirable to synthesize the CAV IL-3 DNA in the form of overlapping oligonucleotides, e.g. overlapping 50-80 mers, which together span the desired coding sequence and contain the cysteine additions desired:

_____ _____ _____ ...
_____ _____ _____ ....

Given a desired coding sequence, the design, synthesis, assembly and ligation, if desired, to synthetic linkers of appropriate oligonucleotides is well within the present level of skill in the art.

EXAMPLE 7

PEGylation of the IL-3 mpCys10 mutein

The mutein human IL-3 mpCys10 was prepared in accordance with Example 5 above and PEGylated with two PEG 5000 derivatives, S-Pyridyl Monomethoxy PEG 5000 and Maleimido Monomethoxy PEG 5000.

a. PEGylation with S-Pyridyl Monomethoxy PEG 5000: a reducible linkage

1. Preparation of the sulfhydryl reactive compound

PEG 5000 was activated for attachment to a sulfhydryl group as follows. 2.0 grams of Monomethoxy PEG 5000 amine was dissolved in 12 ml dry peroxide free, dioxane. 144 mg (15% excess) of N-succinimidyl-3-(2 pyridyldithio) propionate (SPDP) was added as a dry powder and the reaction was allowed to proceed at room temperature. After 24 hours, the S-pyridyl Monomethoxy PEG 5000 product was precipitated using dry, peroxide free diethyl ether and washed with ether. The product was dried under vacuum to obtain 1.92 grams of white solid, which was identified as S-Pyridyl Monomethoxy PEG 5000 by NMR and IR. The PEG 10,000 analog was likewise prepared via an analogous procedure.

2. PEGylation of mutein C10 human IL-3

For this coupling, natural (wild type) human IL-3 was also treated with the PEGylation reagents as a negative control. A stock solution at 1 mg/ml of the mpCys10 mutein in a pH 7 buffered solution of 50 mM NaH$_2$PO$_4$, 100 micro M DTT, 1 mM EDTA and about 3mM Guanidine HCl was used. DTT was added to prevent dimerization of the protein; EDTA was added to prevent dimerization via metal mediated oxidative coupling. Guanidine remains as an artifact of the refolding of the protein. A pH 7 was used; a range of 6.5-7.5 is preferred. 0.9 mg of S-Pyridyl Monomethoxy PEG 5000, prepared as set forth above, was weighed into an eppendorf tube. 360 microliters of the buffered mutein was added and the mixture was vortexed briefly to homogeneity. The reaction was performed at 4 degrees centigrade and when sampled after 2 hours, was found to be complete. Analysis on a 10-20% gradient SDS acrylamide gel showed the product as nearly pure and running at about 28 kD. (By comparison, mpCys10 and its dimer were used as standards and found to migrate to 15 and 30 kD respectively.) A reducing lane on the gel showed that the PEGylated IL-3 mutein is sensitive to reduction by DTT and regenerated the original protein at about 15 kD.

b. PEGylation with Maleimido Monomethoxy PEG 5000: a non-reducible linkage.

1. Preparation of the sulfhydryl reactive compound

In this experiment, PEG 5000 activation was accomplished as follows. 2.0 mg of monomethoxy PEG 5000 amine was dissolved in 12 ml of dry, peroxide free dioxane. 154 mg of sulfosuccinimidyl 4-(N-maleimidomethyl) cyclohexane-1-carboxylate (SMCC) (15% excess) was added as a dry powder and the reaction was allowed to proceed at room temperature. After 24 hours, work up of the product was carried out in the same manner as the S-Pyridyl Monomethoxy PEG 5000 to obtain 1.82 grams Maleimido Monomethoxy PEG 5000. The PEG 10,000 analog was prepared similarly.

2. PEGylation of the cys10 IL-3 mutein

This reaction was carried out in the same manner as the PEGylation reaction using the reducible PEG 5000 reagent and with natural human IL-3 as a negative control. However, 1.0 mg of the PEG derived PEGylating agent Maleimido Monomethoxy PEG 5000 was used. 400 microliters of the mpCys10 IL-3 mutein was added and vortexed to homogeneity. At t=2 hours the reaction was found to be complete. The product was nearly pure and indistinguishable from the S Pyridyl derived conjugate in molecular weight. However, this product is perfectly inert to reductive conditions, such as DTT; in this reducing lane the product, at 28 kD, persists.

In both control reactions, nothing indicative of conjugation is evident at 2 hrs or even at 24 hrs. Selectivity for accessible sulfhydryls in this chemistry is therefore very high.

EXAMPLE 8

PEGylation of multiple cysteine muteins m3Cys9,10 and m3Cys6,10

In this experiment, protein stock for both muteins was at 300 µg/ml in the phosphate buffer solution, as described in Example 7. PEGylation stock solutions consisted of the S-pyridyl or Maleimide activated PEG 5000 polymers at 50 µg/ml in the same buffer. To initiate the reaction, 11 µl of the appropriate PEG stock was added to 100 µl of the appropriate protein stock (either the m3Cys9,10 mutein or the m3Cys6,10 mutein) while vortexing. Reactions were allowed to proceed at 4 degrees centigrade overnight. SDS gel analysis of the products as described above revealed that only a trace of starting material remained with both chemistries. Furthermore, both chemistries resulted in new products with a gel mobility of about 37 kD. Reducing lanes on this same gel show that the maleimide conjugate is resistant to reducing, while the S-Pyridyl derived conjugate reverts to starting material.

EXAMPLE 9

Screening of novel CAVs

Having the constructed novel DNA molecules encoding CAVs in the appropriate expression vector and having attached the sulfhydryl reactive compound to the muteins, it may be desirable to produce each CAV protein on a small scale and "screen" for muteins which possess the desired attachment site or sites. The biological activity of each CAV, before and after attachment of the sulfhydryl reactive compound can be rapidly assessed using an in vitro assay.

Small scale bacterial production of CAV muteins

Bacterial strain GI586 was transformed with purified plasmid DNAs consisting of bacterial expression vector, pAL-hIL3-781, ATCC Accession Number 67932, with novel CAV IL-3 coding sequences The transformed cells were spread on LB agar plates containing 50 µg/ml ampicillin at a density to yield approximately 100 colonies per plate. 3 ml of L broth plus 50 µg/ml ampicillin was inoculated with a single bacterial colony and grown overnight at 30 degrees centigrade. 50 ml of induction media (0.1×L Broth, 1×M9 salts, 0.4% glucose, 1 mM MgSO$_4$, 50 µg/ml ampicillin) was inoculated with 1 ml of the overnight culture. The 50 ml culture was grown with aeration at 30 degrees centigrade until an 0.5 OD 600 nm level was reached, then the temperature was shifted to 40 degrees centigrade and growth continued for at least 2 hours.

Cells were then harvested by centrifugation at 3500 rpm for minutes in a Sorval centrifuge with a 3B rotor. The supernatant was discarded and the cell pellet resuspended in 1 ml of buffer PED (50 mM NaH$_2$PO$_4$, pH 7.0, 1 mM EDTA, 5mM DTT, 10 mM PMSF). This 1 ml solution was passed twice through a French Press at 10,000 psi and kept on ice. The solution was then microfuged for 5 minutes at 12,000 rpm. The supernatant was discarded and the pelleted material was resuspended in 150 µl of 7M guanidine-HCl in PED buffer The solution was then diluted with 650 µl of PED buffer and placed in dialysis tubing (10,000 MWCO Spectrapore) The sample was dialyzed for at least 4 hours against 2 liters of PED.1 buffer (50 mM NaH$_2$PO$_4$ pH 7.0, 1 mM EDTA, 0.1 mM DTT). The sample was collected and microfuged to remove precipitated proteins. The sample was then analyzed on a 12% Laemmli SDS PAGE gel and the amount of IL-3 protein estimated.

The protein solution was then concentrated to about 0.5 mg/ml, and 200 µg was reacted with a 15 fold molar excess of either S-Pyridyl Monomethoxy PEG 5000 or Maleimido Monomethoxy PEG 5000 for several hours at 4 degrees centigrade. The products were then analyzed by SDS PAGE and biological activity determined by an in vitro TF-1 cell proliferation assay.

Alternatively, this small scale production for screening may be carried out before attachment of the sulfhydryl reactive compound. In that case, biological activity may still be determined by an in vitro TF-1 cell proliferation assay and the products may be analyzed by SDS PAGE analysis, in accordance with known techniques.

The same or similar procedures may be used by one skilled in the art to attach other sulfhydryl reactive compounds to the other CAVs of the invention Homogeneity can be observed by conventional analysis of the modified CAVs so produced e.g. using standard SDS-PAGE or HPLC analysis.

Numerous modifications may be made by one skilled in the art to the methods and compositions of the present invention in view of the disclosure herein Such modifications are believed to be encompassed by this invention as defined by the appended claims

We claim:

1. A cysteine added variant of human interleukin-3 characterized by having an added cysteine residue in the N-terminal region between amino acids 1 through 14 of the natural human interleukin-3 sequence, said added cysteine residue either being substituted for an amino acid in the natural human interleukin-3 sequence or being inserted between two amino acids of the natural human interleukin-3 sequence, said cysteine added variant being further characterized by having a polyethylene glycol moiety covalently attached to said added cysteine residue.

2. A cysteine added variant of claim 1 wherein said added cysteine residue is located in the N-terminal region between amino acids 6 through 12 of the natural human interleukin-3 sequence.

3. A cysteine added variant of claim 2, further characterized by having an N-terminal commencing with methionine and the deletion of alanine at position 1 of the natural human interleukin-3.

4. A cysteine added variant of claim 3 wherein said cysteine residue is substituted for the serine residue at position 8 of the natural human interleukin-3 sequence.

5. A cysteine added variant of claim 3 wherein said cysteine residue is substituted for the lysine at position 10 of the natural human interleukin-3 sequence.

6. A cysteine added variant of claim 2, further characterized by having an N-terminus modified by the deletion of alanine and proline at positions 1 and 2 of the natural human interleukin-3.

7. A pharmaceutical composition for stimulating hematopoiesis comprising a therapeutically effective amount of a cysteine added variant of claim 1 or claim 4 in admixture with a pharmaceutically acceptable carrier.

8. The composition of claim 7 wherein said polyethylene glycol moiety has a molecular weight of about 1,000 to about 30,000.

9. A method of producing a cysteine added variant of claim 1 comprising covalently attaching said polyethylene glycol moiety to said added cysteine residue of said cysteine added variant, produced by culturing a host cell containing and capable of expressing a DNA sequence encoding said cysteine added variant.

* * * * *